(12) United States Patent
Teicher

(10) Patent No.: US 9,050,032 B2
(45) Date of Patent: Jun. 9, 2015

(54) METHODS FOR MEASURING THE MAGNITUDE OF ATTENTION AND MOTOR ACTIVITY DISTURBANCE IN A SUBJECT

(75) Inventor: Martin Teicher, Rye, NH (US)

(73) Assignee: The McLean Hospital Corporation, Belmont, MA (US)

( * ) Notice: Subject to any disclaimer, the term of this patent is extended or adjusted under 35 U.S.C. 154(b) by 1005 days.

(21) Appl. No.: 13/122,805

(22) PCT Filed: Oct. 8, 2009

(86) PCT No.: PCT/US2009/060021
§ 371 (c)(1),
(2), (4) Date: May 11, 2011

(87) PCT Pub. No.: WO2010/042730
PCT Pub. Date: Apr. 15, 2010

(65) Prior Publication Data
US 2011/0208439 A1    Aug. 25, 2011

Related U.S. Application Data

(60) Provisional application No. 61/195,576, filed on Oct. 8, 2008.

(51) Int. Cl.
*G01N 33/48* (2006.01)
*G01N 33/50* (2006.01)
*A61B 5/11* (2006.01)
*A61B 5/16* (2006.01)

(52) U.S. Cl.
CPC ............. *A61B 5/1118* (2013.01); *A61B 5/1127* (2013.01); *A61B 5/165* (2013.01); *A61B 5/168* (2013.01)

(58) Field of Classification Search
USPC .................................... 702/19; 600/300, 558
See application file for complete search history.

(56) References Cited

U.S. PATENT DOCUMENTS

| 2003/0233032 | A1* | 12/2003 | Teicher et al. | ................ 600/300 |
| 2004/0220493 | A1* | 11/2004 | Teicher et al. | ................ 600/558 |
| 2008/0220400 | A1  | 9/2008  | Cox et al.    |                        |

FOREIGN PATENT DOCUMENTS

| WO | WO-03/073212 A2  | 9/2003 |
| WO | WO-2006/029021 A2 | 3/2006 |

OTHER PUBLICATIONS

International Search Report for International Application No. PCT/US2009/60021, mailed Dec. 9, 2009.
Written Opinion for International Application No. PCT/US2009/60021, mailed Dec. 9, 2009.
Communication enclosing the Extended European Search Report for European Application No. 09819888.0, dated Nov. 22, 2012.

(Continued)

*Primary Examiner* — Toan Le
*Assistant Examiner* — Manuel Rivera Vargas
(74) *Attorney, Agent, or Firm* — Clark & Elbing LLP

(57) ABSTRACT

The invention features methods and systems to monitor changes in the magnitude of attentional disturbance and the magnitude of motor activity disturbance in a subject. The invention also features methods and systems for determining a subject's degree of concordance with individuals having an attentional disorder versus individuals not having an attentional disorder. The methods and systems of the invention can enable clinicians and consumers to ascertain both the severity of an attentional disorder as well as how much an individual changes over time, or with therapy.

32 Claims, 13 Drawing Sheets

(56) References Cited

OTHER PUBLICATIONS

Tabori-Kraft et al., "Is OPTAx useful for monitoring the effect of stimulants on hyperactivity and inattention? A brief report," *Eur Child Adolesc Psychiatry* 16: 347-351, 2007.

Teicher M H et al., "Objective measurement of hyperactivity and attentional problems in ADHD," *J. Am. Acad. Child Adolesc. Psychiatry* 35: 334-42, 1996.

European Search Report for European Patent Application No. 13196104.7, mailed Feb. 18, 2014 (8 pages).

* cited by examiner

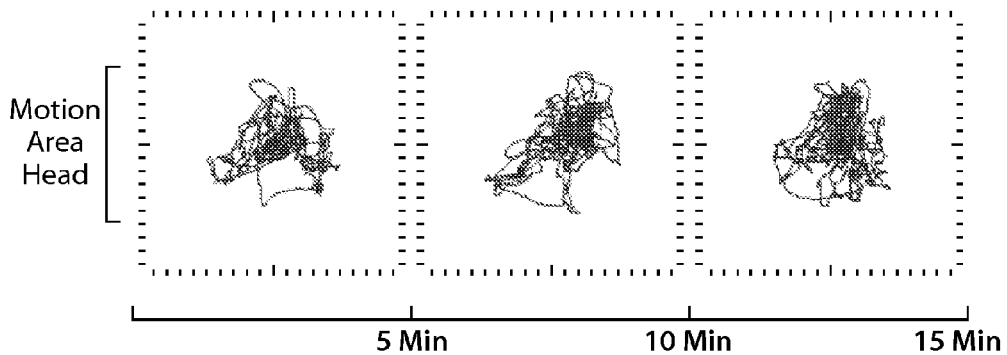

| Measure | Reflector Location | Results | Reference Range (16-84 Percentile) | Age Percentile (t ≤ 16 Age Percentile) |
|---|---|---|---|---|
| Immobility Duration: *(milliseconds)* The average amount of time spent sitting still. | Head | 57 | 83 - 271 | 1$^t$ |
| Movements: *(number)* The number of position changes. | Head | 5444 | 1037 - 3321 | 1$^t$ |
| Displacement: *(meters)* The total distance moved by the marker. | Head | 10.12 | 1.33 - 4.87 | 2$^t$ |
| Area: *(centimeters squared)* The total area covered by the marker's path. | Head | 376 | 26 - 131 | 1$^t$ |
| Spatial Complexity: *(scale score)* The complexity of the movement path. Lower values indicate linear or back-and-forth movement. Higher values indicate more complex movement. | Head | 1.042 | 1.088 - 1.305 | 1$^t$ |
| Temporal Scaling: *(scale score)* The pattern of movement in time. Lower value indicate lack of movement. Higher values indicate incessant movement. | Head | 0.932 | 0.394 - 0.86 | 9$^t$ |

Fig. 2A

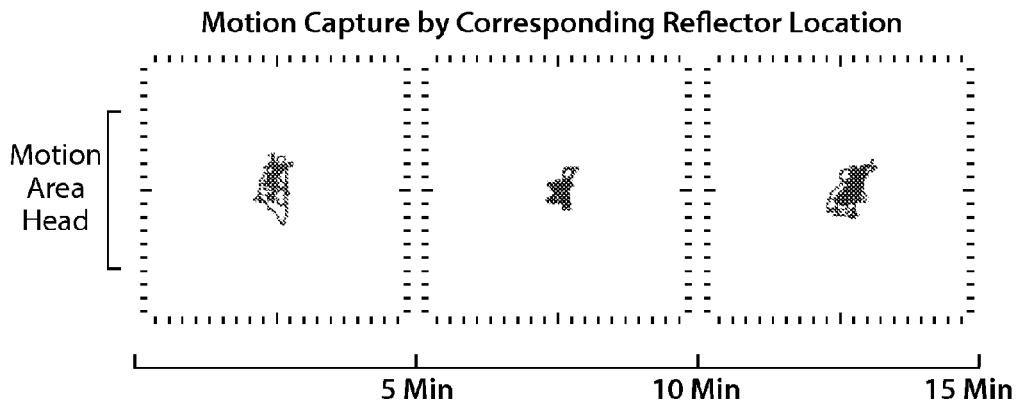

| Measure | Reflector Location | Results | Reference Range (16-84 Percentile) | Age Percentile (t ≤ 16 Age Percentile) |
|---|---|---|---|---|
| Immobility Duration: (milliseconds) The average amount of time spent sitting still. | Head | 179 | 83 - 271 | 63 |
| Movements: (number) The number of position changes. | Head | 1763 | 1037 - 3321 | 55 |
| Displacement: (meters) The total distance moved by the marker. | Head | 2.5 | 1.33 - 4.87 | 53 |
| Area: (centimeters squared) The total area covered by the marker's path. | Head | 67 | 26 - 131 | 41 |
| Spatial Complexity: (scale score) The complexity of the movement path. Lower values indicate linear or back-and-forth movement. Higher values indicate more complex movement. | Head | 1.145 | 1.088 - 1.305 | 40 |
| Temporal Scaling: (scale score) The pattern of movement in time. Lower value indicate lack of movement. Higher values indicate incessant movement. | Head | 0.476 | 0.394 - 0.86 | 70 |

Fig. 2B

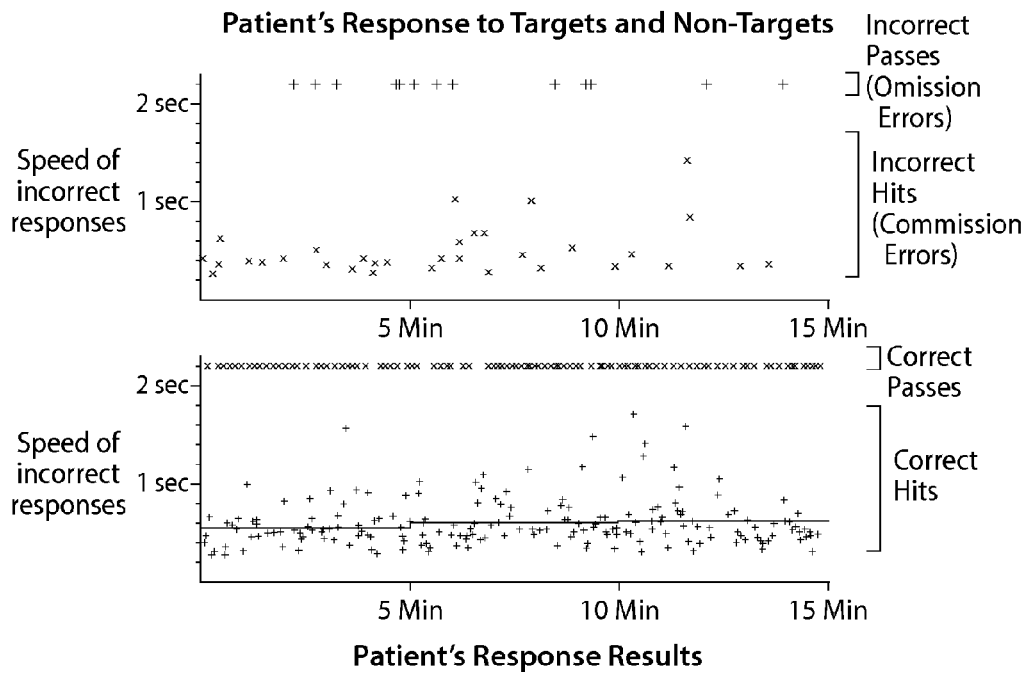

Patient's Response Results

| Measure | Results | Reference Range (16-84 Percentile) | Age Percentile (t ≤ 16 Age Percentile) |
|---|---|---|---|
| Accuracy: (percent) The percentage of correct responses. | 89.1 | 70.4 - 95.6 | 54 |
| Omission Errors: (percent) The percentage of missed targets (a measure of inattention). | 7.1 | 0.4 - 13.7 | 25 |
| Commission Errors: (percent) The percentage of incorrect responses to non-targets (a measure of impulsivity). | 14.5 | 7.9 - 46.9 | 65 |
| Latency: (milliseconds) The average amount of time to respond correctly (speed). | 591 | 371.6 - 546.6 | 92 |
| Variability: (milliseconds) The variation in response time to the correct target. | 241 | 91.6 - 186.6 | 8$^t$ |
| C.O.V. (number) A normalized measure of response time variation. | 40 | 20.3 - 40.3 | 16$^t$ |

Fig. 3A

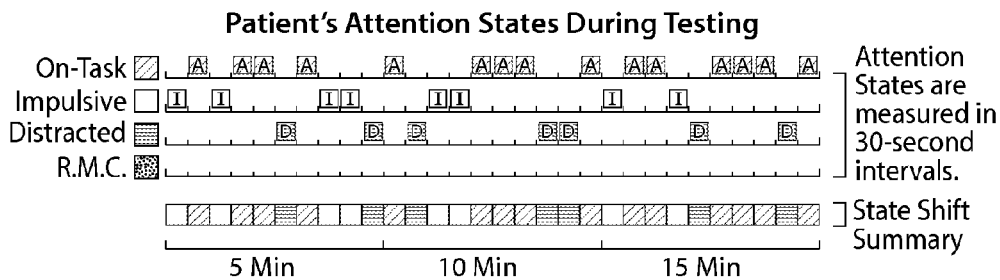

Patient's Attention States During Testing

Attention States are measured in 30-second intervals.

State Shift Summary

Attention State Results

| Measure | Results | Reference Range (16-84 Percentile) | Age Percentile (t ≤ 16 Age Percentile) |
|---|---|---|---|
| Number of Shifts: *(number)* A measure of how many times a change in behavioral states occurs over the course of a test. | 20 | 6 - 17 | 8$^t$ |
| On-Task: *(percent)* Percent of 30 second blocks in which subjects performed with very high level of accuracy. | 50 | 6.7 - 86.7 | 47 |
| Impulsive: *(percent)* Percent of blocks when subjects performed better than chance but made a significant number of commission errors. | 26.7 | 6.7 - 55 | 55 |
| Distracted: *(percent)* Percent of blocks when subjects performed better than chance but missed a significant number of targets. | 23.3 | 0 - 16.7 | 7$^t$ |
| R. Random: *(percent)* Percent of blocks when subjects performed no better than predicted by random chance. | 0 | 0 - 23.3 | 99 |
| M. Minimal: *(percent)* Percent of blocks when subjects performed no better than predicted by random chance and made few responses. | 0 | 0 - 3.3 | 99 |
| C. Contrary: *(percent)* Percent of blocks when subjects performed worse than predicted by random chance. | 0 | 0 - 0 | 99 |

Fig. 4A

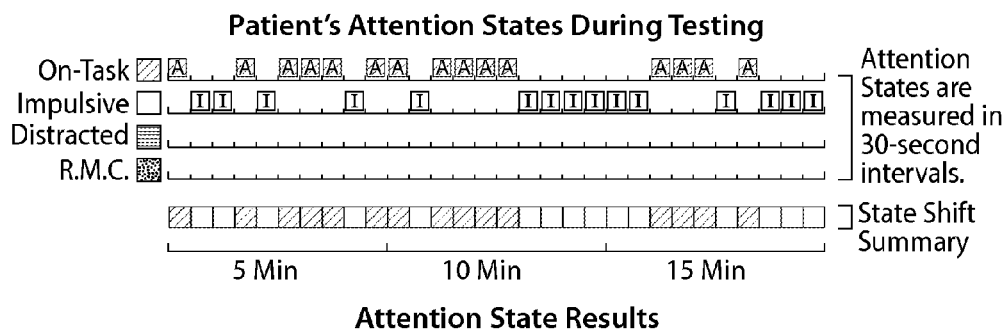

Attention State Results

| Measure | Results | Reference Range (16-84 Percentile) | Age Percentile (t ≤ 16 Age Percentile) |
|---|---|---|---|
| Number of Shifts: *(number)* A measure of how many times a change in behavioral states occurs over the course of a test. | 13 | 6 - 17 | 51 |
| On-Task: *(percent)* Percent of 30 second blocks in which subjects performed with very high level of accuracy. | 50 | 6.7 - 86.7 | 47 |
| Impulsive: *(percent)* Percent of blocks when subjects performed better than chance but made a significant number of commission errors. | 50 | 6.7 - 55 | 23 |
| Distracted: *(percent)* Percent of blocks when subjects performed better than chance but missed a significant number of targets. | 0 | 0 - 16.7 | 99 |
| R. Random: *(percent)* Percent of blocks when subjects performed no better than predicted by random chance. | 0 | 0 - 23.3 | 99 |
| M. Minimal: *(percent)* Percent of blocks when subjects performed no better than predicted by random chance and made few responses. | 0 | 0 - 3.3 | 99 |
| C. Contrary: *(percent)* Percent of blocks when subjects performed worse than predicted by random chance. | 0 | 0 - 0 | 99 |

Fig. 4B

QUOTIENT ADHD SYSTEM RESULTS

The Quotient ADHD System Index includes 19 indices, 6 for motion and 13 for attention. The resulting index score summarizes the degree of agreement between the Quotient ADHD Test results of this patient and ADHD patients.

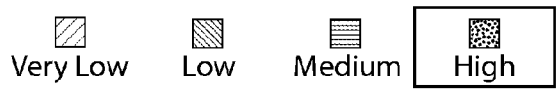

QUOTIENT ADHD SYSTEM SCALED SCORES

The Quotient ADHD System Scaled Score consists of:
- Motion Scaled Score - a composite of how this patient's motion compares to the community sample.
- Attention Scaled Score - a composite of how this patient's attention compares to the community sample.
- Global Scaled Score - demonstrates the combination of indices for this patient as compared to the community sample High scaled scores are associated with the scores that ADHD patients receive.

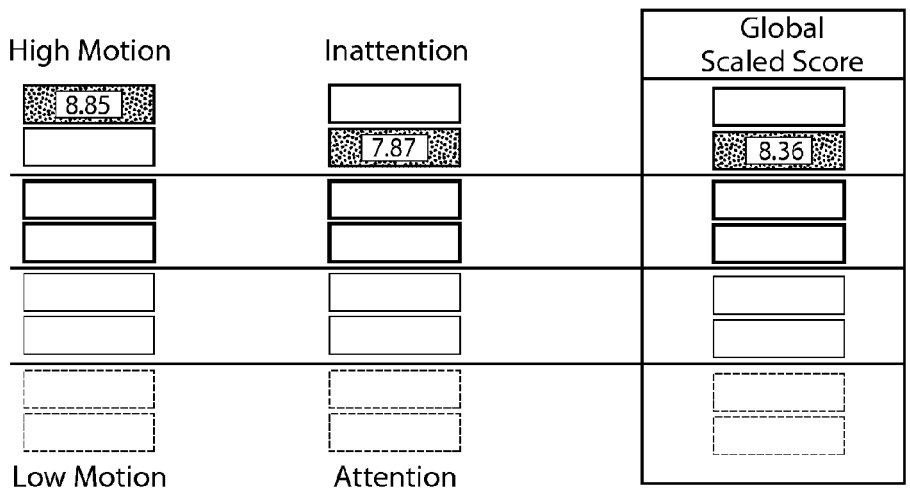

Fig. 5A

QUOTIENT ADHD SYSTEM RESULTS

The Quotient ADHD System Index includes 19 indices, 6 for motion and 13 for attention. The resulting index score summarizes the degree of agreement between the Quotient ADHD Test results of this patient and ADHD patients.

Very Low | Low | Medium | High

QUOTIENT ADHD SYSTEM SCALED SCORES

The Quotient ADHD System Scaled Score consists of:
- Motion Scaled Score - a composite of how this patient's motion compares to the community sample.
- Attention Scaled Score - a composite of how this patient's attention compares to the community sample.
- Global Scaled Score - demonstrates the combination of indices for this patient as compared to the community sample High scaled scores are associated with the scores that ADHD patients receive.

| High Motion | Inattention | Global Scaled Score |
|---|---|---|
|  |  |  |
|  |  |  |
|  |  |  |
|  |  |  |
| 4.5 |  | 3.9 |
|  | 3.31 |  |
|  |  |  |
|  |  |  |
| Low Motion | Attention |  |

Fig. 5B

METHODS FOR MEASURING THE MAGNITUDE OF ATTENTION AND MOTOR ACTIVITY DISTURBANCE IN A SUBJECT

CROSS-REFERENCE TO RELATED APPLICATIONS

This application is the U.S. national stage filing under 35 U.S.C. §371 of international application PCT/US2009/060021, filed Oct. 8, 2009, which claims benefit of the filing date of U.S. Provisional Application No. 61/195,576, filed Oct. 8, 2008.

BACKGROUND OF THE INVENTION

The invention relates to methods and systems for the diagnosis and management of attentional disorders.

Alterations in locomotor-activity levels and disturbances in rest-activity rhythms have long been recognized as an integral sign of many psychiatric disorders. For example, the hyperactivity of children with Attention-Deficit/Hyperactivity Disorder (ADHD) is most readily discernible as a failure to inhibit motor activity to low-levels.

Using precisely quantified movements, ADHD children have been shown to move their head 2.3 times more often than normal children, moved 3.4 times as far, cover a 3.8-fold greater area, and have a more linear and less complex movement pattern. Teicher et al., J. Am. Acad. Child Adolesc. Psychiatry 35:334 (1996). ADHD children also have disturbances in their ability to perform on cognitive control tasks. These disturbances can be reflected in conventional measures of performance such as accuracy, omission and commission errors and response latency, along with measures of fluctuation in attention states. Teicher et al., J. Child Adolesc. Psychiatry 14:219 (2004).

The problem is that dozens of measures have been described that quantify aspects of attention and activity. From this array of potential measures it is unclear which measures should be used for clinical purposes. There is a need for reliable, inexpensive, and easy to use methods to derive a small number of omnibus composite measures that are most suitable for diagnosing attentional disorders and for assessing how subjects change over time and with therapy.

Previous attempts have been made to provide a reduced number of composite scores. The Conners' CPT-II test provides a single composite called the Confidence Index that suggests closeness of the match to a clinical or non-clinical profile. This composite index uses only attention variables, and has been reported in independent samples to fail to distinguish between children with and without ADHD (Edwards et al., J. Abnorm. Child Psychol. 35:393 (2007)). Similarly, it has been reported to fail to distinguish between adults with and without ADHD (Solanto et al., CNS Spectr. 9:649 (2004)).

The McLean Motion and Attention Test (M-MAT) used principal component analysis (PCA) to reduce the number of activity and attention measures. From all 6 activity measures two composites were derived ("hyperactivity", "movement area"), and 4 composites were derived from all 6 attention measures ("inattention", "impulsivity", "latency", "variability"). While this approach reduced the number of measures, it did not do so to a sufficient degree. Further, applying PCA separately to a moderate number of activity and attention performance measures does not yield composites that are optimal as treatment-responsive measures of attention disturbance and motor activity disturbance. This is because the distribution of scores for the populations normal and abnormal subjects obtained using these M-MAT composites do not provide enough differential between typical ADHD subjects and typical non-ADHD subjects and too much of the dynamic range of the M-MAT composite curve is dictated by extreme scores, rather than the range between normal and abnormal (e.g., the range in which partially treated subjects would be found). As a result, the M-MAT composite score is insensitive to change in a subject (i.e., such as a modest improvement resulting from therapy, or a change in the subject over time). Moreover, the M-MAT composites are not bounded between set limits and are not scaled in a way that is readily interpretable clinically.

SUMMARY OF THE INVENTION

The invention features methods and systems to monitor changes in the magnitude of attentional disturbance and the magnitude of motor activity disturbance in a subject. The invention also features methods and systems for determining a subject's degree of concordance with individuals having an attentional disorder versus individuals not having an attentional disorder. The methods and systems of the invention can enable clinicians and consumers to ascertain both the severity of an attentional disorder as well as how much an individual changes over time, or with therapy.

In a first aspect, the invention features a method for evaluating a subject, the method including: (a) testing the subject to produce test data; and (b) transmitting the test data to a computer for analysis, wherein the analysis includes (i) extracting from the test data values for responsive attention metrics and values for responsive motor activity metrics; (ii) calculating from the responsive attention metrics the magnitude of attention disturbance in the subject; (iii) calculating from the responsive motor activity metrics the magnitude of motor activity disturbance in the subject; and (iv) on the basis of the magnitude of attention disturbance and the magnitude of motor activity disturbance evaluating the subject.

The invention also features a method for evaluating a subject, the method including: (a) providing data having been collected by testing the subject to produce test data; and (b) performing an analysis, the analysis including (i) extracting from the test data values for responsive attention metrics and values for responsive motor activity metrics; (ii) calculating from the responsive attention metrics the magnitude of attention disturbance in the subject; (iii) calculating from the responsive motor activity metrics the magnitude of motor activity disturbance in the subject; and (iv) on the basis of the magnitude of attention disturbance and the magnitude of motor activity disturbance evaluating the subject.

In any of the above aspects, the testing can include measuring the activity of the subject using an infrared motion analysis system by tracking the movements of the subject's head, leg, or foot using a camera and the test data includes motor activity data.

In any of the above aspects, the testing can include performing an attentional test on the subject and the test data includes attentional data. In certain embodiments, the analysis includes assessing the fluctuation in attentional states of the subject.

In any of the above aspects, the method can further include calculating from the magnitude of attention disturbance and the magnitude of motor activity disturbance a global composite score; and on the basis of the global composite score evaluating the subject.

The invention further features a report providing an evaluation for a subject, the report including (i) a magnitude of attention disturbance score for the subject; and (ii) a magnitude of motor activity disturbance score for the subject. The reports of the invention can be fixed in a tangible medium of expression (i.e., recorded on paper, audio tape, in electronic format, or saved on a computer disk). Multiple reports can be made to monitor change in a subject over time, or with therapy.

In one embodiment of the above aspects, the responsive attention metrics are selected from errors of omission, percent time spent in distracted state, percent time spent in minimal response state, accuracy-adjusted latency, and variability in response latency.

In another embodiment of the above aspects, the responsive motor activity metrics are selected from microevents, displacement, and area.

In any of the above aspects, the method can be repeated to observe changes in the magnitude of attention disturbance, the magnitude of motor activity disturbance, or the global composite score of the subject (i.e., changes result from aging, or from therapy). In one particular embodiment, the testing is performed on the subject while unmedicated and while medicated.

In any of the above methods, the magnitude of attention disturbance, the magnitude of motor activity disturbance, or the global composite score can be used to evaluate the efficacy of a therapy.

In certain embodiments, the analysis further includes (x) extracting from the test data values for attention metrics and values for motor activity metrics; (y) calculating from the attention metrics and the motor activity metrics a concordance composite score; and (z) on the basis of the concordance composite score determining the probability of the subject having an attentional disorder.

For example, the concordance composite score can be calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state. The analysis may further include, based upon the concordance composite score, determining whether the subject has the attentional disorder. Alternatively, the analysis can further include classifying the subject on the basis of the probability (i.e., a very low, low, medium, or high probability of the subject having the attentional disorder), or providing a probability from 0% to 100%.

In any of the above methods the attentional disorder can be ADD, ADHD, or Hyperkinetic Disorder, or any other attentional disorder described herein.

The invention further features a system for evaluating a subject, the system including: (a) an input component configured to receive test data for the subject; and (b) a processor provided with a computer program for (i) extracting from the test data values for responsive attention metrics and values for responsive motor activity metrics; (ii) calculating from the responsive attention metrics the magnitude of attention disturbance in the subject; and (iii) calculating from the responsive motor activity metrics the magnitude of motor activity disturbance in the subject.

In certain embodiments of the system, the responsive attention metrics are selected from errors of omission, percent time spent in distracted state, percent time spent in minimal response state, accuracy-adjusted latency, and variability in response latency.

In other embodiments of the system, the responsive motor activity metrics are selected from microevents, displacement, and area.

In still other embodiments, the system includes a processor provided with a computer program for calculating from the magnitude of attention disturbance and the magnitude of motor activity disturbance a global composite score.

In yet another embodiment, the system further includes a processor provided with a computer program for (x) extracting from the test data values for attention metrics and values for motor activity metrics; and (y) calculating from the attention metrics and the motor activity metrics a concordance composite score. For example, the concordance composite score can be calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state.

In a related aspect, the invention features a method for evaluating a subject, the method including: (a) testing the subject to produce test data; (b) transmitting the test data to a computer for analysis, wherein the analysis includes (i) extracting from the test data values for attention metrics and values for motor activity metrics; (ii) calculating from the attention metrics and the motor activity metrics a concordance composite score; and (iii) on the basis of the concordance composite score determining the probability of the subject having an attentional disorder, wherein the concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state.

The invention further features a method for evaluating a subject, the method including: (a) providing data having been collected by testing the subject to produce test data; and (b) performing an analysis, the analysis including (i) extracting from the test data values for attention metrics and values for motor activity metrics; (ii) calculating from the attention metrics and the motor activity metrics a concordance composite score; and (iii) on the basis of the concordance composite score determining the probability of the subject having an attentional disorder, wherein the concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state.

In the above methods, the analysis can further include, based upon the concordance composite score, determining whether the subject has the attentional disorder. In another embodiment, the analysis further includes classifying the subject on the basis of the probability (i.e., a very low, low, medium, or high probability of having the attentional disorder).

In the above methods, the attentional disorder is ADD, ADHD, or Hyperkinetic Disorder, or any other attentional disorder described herein.

The invention further features a system for evaluating a subject, the system including: (a) an input component configured to receive test data for the subject; and (b) a processor provided with a computer program for (i) extracting from the test data values for attention metrics and values for motor activity metrics; and (ii) calculating from the attention metrics and the motor activity metrics a concordance composite score, wherein the concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state.

In an embodiment of the methods, reports, and systems of the invention, the magnitude of attention disturbance is calculated from a composite that includes attention metrics that are indicative of distraction (errors of omission, percent time spent in distracted state, accuracy-adjusted latency, variability in response latency) or diminished effort (percent time spent in minimal response state). In another embodiment of the methods, reports, and systems of the invention, the magnitude of attention disturbance is calculated from a composite that is free of attention metrics that are indicative of impulsivity (e.g., errors of commission, percent time spent in impulsive state), as impulsivity may not be a consequence of impaired attention (e.g., impulsivity can be a consequence of impatience, response strategy, or high degree of tolerance to making errors). Excluding variables that are primarily indicative of impulsivity can enhance both the diagnostic specificity of the composite, and it's degree of responsiveness to treatment.

In certain embodiments of the methods, reports, and systems of the invention, (a) the magnitude of attention disturbance is calculated from a composite that is free of motor activity metrics; (b) the magnitude of attention disturbance is calculated from a composite that comprises at least two, three, four, or five responsive attention metrics; and/or (c) the magnitude of attention disturbance is calculated from a composite including attention metrics, wherein the attention metrics consist of responsive attention metrics.

In certain other embodiments of the methods, reports, and systems of the invention, (a) the magnitude of motor activity disturbance is calculated from a composite that is free of attention metrics; (b) the magnitude of motor activity disturbance is calculated from a composite that comprises at least two or three responsive motor activity metrics; and/or (c) the magnitude of motor activity disturbance is calculated from a composite including motor activity metrics, wherein the motor activity metrics consist of responsive motor activity metrics.

As used herein, the term "attentional disorder" refers to a condition characterized by inattention, over-activity, and/or impulsiveness. The methods and systems of the invention can be useful for diagnosing and/or evaluating change in, such as response to treatment, attentional disorders, such as, without limitation, Attention Deficit Hyperactivity Disorder, Attention Deficit Disorder, and Hyperkinetic Disorder. Attention Deficit Hyperactivity Disorder, which is also referred to in the literature as Attention Deficit Disorder/Hyperactivity Syndrome (ADD/HS), is a condition (or group of conditions) characterized by impulsiveness, distractibility, inappropriate behavior in social situations and hyperactivity. ADD/HS is reported to have a prevalence of 3-9% in children (Anderson et al., Archives of General Psychiatry 44:69 (1987); Bird et al., Archives of General Psychiatry 45:1120 (1988); and Szatmari et al., J. Child Psychol. Psychiatry 30:219 (1989)), and upwards of 18% as reported in recent systemic reviews (Rowland et al., Ment. Retard. Dev. Disabil. Res. Rev. 8:162 (2002)). Symptoms of ADHD often diminish with age, but about 65% of individuals with ADHD continue to experience significant symptoms in adulthood (Faraone et al., Psychol. Med. 36:159 (2006)). This disorder can impair social function, learning and/or development and is therefore now recognized as a serious problem. It is further recognized that many children with ADHD go on to develop other comorbid conditions or social problems in adulthood. In clinical terms ADHD is diagnosed if any one of the three main clinical features of inattention, over-activity and impulsiveness, persists in two or more situations, e.g., in both a home and school environment (American Psychiatric Association. Diagnostic and Statistical Manual of Mental Disorders, Fourth Edition (DSM-IV) Washington D.C.; American Psychiatric Association, 1994). A particularly severe form of ADHD is termed Hyperkinetic Disorder. In Britain, this diagnosis is made only if all three of the main clinical features (inattention, over-activity and impulsiveness) have been present from an early age, persist in more than one situation (e.g., home and school) and impair function (see The ICD-10 Classification of Mental and Behavioural Disorders: Diagnostic Criteria for Research, Geneva: World Health Organisation, 1993: 155-7). Reports indicate that 1.4% of children suffer from hyperkinetic disorder (Meltzer H, Gatward R, Goodman R, Ford T. Mental Health of Children and Adolescents in Great Britain. ONS. London: The Stationery Office; 2000).

As used herein, the terms "test" and "testing" refer to motor activity tests and testing and attentional tests and testing.

As used herein, the term "motor activity test" refers to a test in which the motor activity of a subject is monitored. For example, movement patterns can be analyzed using procedures described by Teicher et al., J. Am. Acad. Child Adolesc. Psychiatry 35:334 (1996). Changes in motor activity can be a measure of the efficacy of a particular drug for the treatment of an attentional disorder (see, for example, PCT Publication No. WO07/114901). The metrics extracted from the data from a motor activity test are referred to herein as "motor activity metrics."

As used herein, the term "attentional test" refers to a cognitive control task which measures the ability to suppress inappropriate thoughts and actions in favor of more appropriate ones. Such tasks include stop signal, Go/No-Go, and Stroop paradigm tasks (see, for example, Casey et al., Am J Psychiatry 164:11 (2007)). In certain embodiments, the attentional test is a continuous performance test (i.e., a CPT test, such as a visual or audio test, see PCT Publication No. WO 2006/023964), given either simultaneously or concurrently with the motor activity monitoring. In some instances, the protocol of the invention includes assessing the fluctuation in attentional states of the subject from the CPT test data. Other attentional measures (i.e., attentional data), such as changes in response latency, response variability, adjusted latency, or adjusted accuracy (see, e.g., U.S. Patent Publication No. 20030233032) are known in the art and may also be used. The metrics extracted from the data from an attentional test are referred to herein as "attention metrics."

As used herein, "assessing the fluctuation in attentional states" refers to measuring the fluctuation in the attentional state of the subject during a test period. The methodology for making such a measurement is described in U.S. Pat. No. 6,685,652, incorporated herein by reference. Briefly, during an attentional test, such as a CPT test or another cognitive control task, the subject's responses are scored. Rather than measure the average attentional state of the subject, the data for a single test is divided into segments and each segment is separately scored to determine how the attentional state of the subject fluctuates during the single test (i.e., the amount of time spent in a particular attentional state (attentive, impulsive, distracted) can be calculated along with the number of shifts in the attentional state of the subject during the test period.

As used herein, "responsive attention metrics" refers to attention metrics that are responsive to therapeutic treatment in a graded manner and which vary in value by at least 15% in fully treated abnormal subjects in comparison to their scores while unmedicated. Responsive attention metrics can be identified by comparing, for any given attention metric, the values obtained for abnormal subjects when medicated and when unmedicated. For example, responsive attention metrics include, without limitation, errors of omission, percent time spent in distracted state, percent time spent in minimal response state, accuracy-adjusted latency, and variability in response latency. The responsive attention metrics are useful for measuring the magnitude of attention disturbance in a subject, and for monitoring changes in the magnitude of attention disturbance in a subject over time and in response to therapy.

As used herein, "responsive motor activity metrics" refers to motor activity metrics that are responsive to therapeutic treatment in a graded manner and which vary in value by at least 25% in fully treated abnormal subjects in comparison to their scores while unmedicated. Responsive motor activity metrics can be identified by comparing, for any given motor activity metric, the values obtained for abnormal subjects when medicated and when unmedicated. For example, responsive motor activity metrics include, without limitation, microevents, displacement, and head area. The responsive motor activity metrics are useful for measuring the magnitude of motor activity disturbance in a subject, and for monitoring changes in the magnitude of motor activity disturbance of a subject over time and in response to therapy.

As used herein, "magnitude of attention disturbance" refers to a score calculated from a composite formula that scores a subject according to attention performance and (i) utilizes responsive attention metrics (e.g., errors of omission, percent time spent in distracted state, percent time spent in minimal response state, accuracy-adjusted latency, and variability in response latency); (ii) is scaled to two bounds (e.g., 0 to 1, 0 to 10, 0 to 100); (iii) includes age and gender as covariates to produce a score appropriate for the subject's age and gender; (iv) is responsive to medication in an abnormal subject in a graded manner; and (v) has a large dynamic range between normal and abnormal subjects, such that the difference in the mean of the distributions of magnitude of attention disturbance scores for normal and untreated abnormal subjects divided by the theoretical range of the bounded scale (i.e., ([mean abnormal−mean normal]/range) ratio is at least 0.20, 0.23, or 0.25 (see FIG. 9), or [mean abnormal−mean normal] is at least 20%, 23%, or 25% (or in the range of 20 to 50%, 20 to 40%, 20 to 30%, 23 to 40%, 25 to 40%, or 25 to 35%) of the theoretical range for a bounded scale, or 25% (or in the range of 25 to 50%, 25 to 40%, or 25 to 35%) of the observed range (±6 standard deviations derived from a sample with at least 40 normal subjects and 40 abnormal subjects) for a non-bounded scale. While the magnitude of attention disturbance score provides a poorer differential diagnosis of an attentional disorder (see FIG. 6), the magnitude of attention disturbance score is very sensitive to degree of change in the subject. Thus, the magnitude of attention disturbance score is useful for treatment planning, and for monitoring and guiding therapeutic decisions. In the composite of formula (2), the parameters (multipliers) were used to adjust the contribution of the responsive attention metrics, and the covariate effects of age and gender derived from non-linear least-squares regression, in which sum squared error was minimized between the magnitude of attention disturbance score and the averaged age and gender based percentiles for the responsive attention metrics used. The average percentile score provided an initial score target for curve fitting, with the logistic regression affording a superior solution having a greater ability to quantify the effects of medication (i.e., methylphenidate) in a subject. The composite of formula (2) has, by design, a sigmoidal dose-response curve relationship relating the responsive attention metrics to the composite outcome in a manner that recognizes clinically meaningful changes in a subject (see FIG. 7). The composite of formula (2) also has by design minimal and maximal response boundaries. These two criteria can be met by using probit, logit or logistic functions, among others.

As used herein, "magnitude of motor activity disturbance" refers to a score calculated from a composite formula that scores a subject according to motor activity performance and (i) utilizes responsive motor activity metrics (e.g., microevents, displacement, and area); (ii) is scaled to two bounds (e.g., 0 to 1, 0 to 10, 0 to 100); (iii) includes age and gender as covariates to produce a score appropriate for the subject's age and gender; (iv) is responsive to medication in an abnormal subject in a graded manner; and (v) has a large dynamic range between normal and abnormal subjects, such that the difference in the mean of the distributions of magnitude of motor activity disturbance scores for normal and untreated abnormal subjects divided by the theoretical range of the bounded scale (i.e., ([mean abnormal−mean normal]/range) ratio is at least 0.20, 0.23, 0.25, or 0.27 (see FIG. 9), or [mean abnormal−mean normal] is at least 20%, 23%, 25%, or 27% (or in the range of 20 to 50%, 20 to 40%, 20 to 30%, 23 to 40%, 25 to 40%, or 25 to 35%) of the theoretical range for a bounded scale, or 25% or 30% (or in the range of 25 to 50%, 25 to 40%, 30 to 50%, 30 to 40%, or 25 to 35%) of the observed range (±6 standard deviations derived from a sample with at least 40 normal subjects and 40 abnormal subjects) for a non-bounded scale. While the magnitude of motor activity disturbance score provides a poorer differential diagnosis of an attentional disorder (see FIG. 6), the magnitude of motor activity disturbance score is very sensitive and responsive to degree of change in the subject. Thus, the magnitude of motor activity disturbance score is useful for treatment planning, and for monitoring and guiding therapeutic decisions. In the composite of formula (3), the parameters (multipliers) were used to adjust the contribution of the responsive motor activity metrics, and the covariate effects of age and gender derived from non-linear least-squares regression, in which sum squared error was minimized between the magnitude of motor activity disturbance score and the averaged age and gender based percentiles for the responsive motor activity metrics used. The average percentile score provided an initial score target for curve fitting, with the logistic regression affording a superior solution having a greater ability to quantify the effects of medication (i.e., methylphenidate) in a subject. The composite of formula (3) has, by design, a sigmoidal dose-response curve relationship relating the responsive motor activity metrics to the composite outcome in a manner that recognizes clinically meaningful changes in a subject (see FIG. 7). The composite of formula (3) also has by design minimal and maximal response boundaries. These two criteria can be met by using probit, logit or logistic functions, among others.

As used herein, "global composite score" refers to a composite value calculated from (i) the magnitude of attention disturbance and (ii) the magnitude of motor activity disturbance. For example, the global composite score can be an average, or a weighted average of the magnitude of attention disturbance and the magnitude of motor activity disturbance. The global composite score is a measure of the overall severity of hyperactivity and inattention in a subject.

As used herein, the term "partially treated abnormal subjects" refers to a population of abnormal subjects exhibiting a partial response to a therapeutic agent (e.g., atomoxetine). These subjects are identified using the ADHD Rating Scale IV (see DuPaul G. J. "ADHD Rating Scale-IV: Checklists, Norms, and Clinical Interpretation." New York, N.Y.: Guilford Press, 1998) in a test administered and scored by a clinician. Partially treated abnormal subjects (i) are symptomatic individuals with ADHD having an ADHD Rating Scale-IV score of ≥25 while unmedicated; and (ii) in response to a particular dose of a medication exhibit a 25% to 40% reduction in ADHD Rating Scale-IV score in comparison to the subject's unmedicated score (i.e., exhibit a 'partial response'). The magnitude composites of the invention (i.e., global composite score, magnitude of attention disturbance, and magnitude of motor activity disturbance) are designed to produce a graded response to therapy and this can be observed in the distribution of scores observed for normal, abnormal, and partially treated abnormal subjects. The magnitude composites also reduce an unwieldy number of individual objective measures into a small number of treatment-responsive, highly reliable, objective composite measures.

As used herein, the term "fully treated abnormal subjects" refers to a population of abnormal subjects exhibiting a full response to a therapeutic agent (e.g., atomoxetine). These subjects are identified using the ADHD Rating Scale IV (see DuPaul G. J. "ADHD Rating Scale-IV: Checklists, Norms, and Clinical Interpretation." New York, N.Y.: Guilford Press, 1998) in a test administered and scored by a clinician. Fully treated abnormal subjects (i) are symptomatic individuals with ADHD having an ADHD Rating Scale-IV score of ≥25 while unmedicated; and (ii) in response to a particular dose of a medication exhibit a ≥41% reduction in ADHD Rating Scale-IV score in comparison to the subject's unmedicated score (i.e., exhibit a 'full response'). In an embodiment of any of the methods and systems of the invention, the magnitude composites of the invention (i.e., global composite score, magnitude of attention disturbance, and magnitude of motor activity disturbance) produce a effect size in the distribution of scores observed for normal subjects and fully treated abnormal subjects of less than 0.2.

As used herein, the term "effect size" refers to a comparison of two groups of subjects for a given composite score (i.e., global composite score, magnitude of attention disturbance, or magnitude of motor activity disturbance) by calculating the difference between the mean values of two groups divided by the pooled standard deviation (i.e., Cohen's D). The magnitude of attention disturbance score can be calculated from a composite formula that has any of the following effect sizes (i) an effect size (Cohen's D) in the distributions of magnitude of attention disturbance scores for normal and untreated abnormal subjects of from 0.5 to 4.0 (e.g., from 0.8 to 4.0, 0.8 to 3.0, 0.8 to 2.5, 0.5 to 2.0, from 0.6 to 2.5, from 0.6 to 2.0, or from 0.6 to 1.6); (ii) an effect size in the distributions of normal and partially treated abnormal subjects of from 0.2 to 0.8 (e.g., from 0.2 to 0.4, from 0.2 to 0.5, from 0.2 to 0.3, 0.25 to 0.4, 0.2 to 0.4, 0.25 to 0.5, or from 0.3 to 0.6); (iii) an effect size in the distributions of partially treated abnormal subjects and abnormal subjects of from 0.2 to 0.8 (e.g., from 0.2 to 0.4, from 0.2 to 0.5, from 0.2 to 0.3, 0.25 to 0.4, 0.2 to 0.4, 0.25 to 0.5, or from 0.3 to 0.6); and/or (iv) an effect size in the distributions of normal subjects and fully treated abnormal subjects of from −0.6 to +0.2. The magnitude of motor activity disturbance score can be calculated from a composite formula that has any of the following effect sizes (a) an effect size (Cohen's D) in the distributions of magnitude of motor activity disturbance scores for normal and abnormal subjects of from 0.8 to 4.0 (e.g., from 0.8 to 4.0, 0.8 to 3.0, 0.8 to 2.5, 0.9 to 2.5, from 1.1 to 2.5, from 1.2 to 2.5, or from 1.3 to 2.5); (b) an effect size in the distributions of normal and partially treated abnormal subjects of from 0.2 to 0.8 (e.g., from 0.2 to 0.6, from 0.2 to 0.5, from 0.2 to 0.4, 0.25 to 0.8, 0.25 to 0.6, 0.25 to 0.5, or from 0.3 to 0.6); (c) an effect size in the distributions of partially treated abnormal subjects and abnormal subjects of from 0.2 to 0.8 (e.g., from 0.2 to 0.6, from 0.2 to 0.5, from 0.2 to 0.4, 0.25 to 0.8, 0.25 to 0.6, 0.25 to 0.5, or from 0.3 to 0.6); and/or (d) an effect size in the distributions of normal subjects and fully treated abnormal subjects of from −0.6 to +0.2.

As used herein, "concordance composite score" refers to a composite value calculated from motor activity metrics and attention metrics (including metrics that are responsive and metrics that are not responsive to therapy as defined herein) using an algorithm that classifies the subject according to their predicted probability, likelihood or odds of belonging to the ADHD group or non-ADHD group. The concordance composite score is a measure of the extent to which the pattern of attention metrics and motor activity metrics for the tested patient correlates with the pattern of metrics for individuals known to have an attentional disorder and individuals known to be normal. The concordance composite score is useful for the differential diagnosis of an attentional disorder, and for classifying a subjects by the probability, likelihood or odds of belonging to the ADHD group versus non-ADHD group (e.g., very low, low, medium, or high degree).

As used herein, "accuracy on the attention test" or "ACC" or "accuracy" refers to the percentage of correct responses during a subject's attentional test.

As used herein, "errors of omission" or "EOM" or "omission errors" refers to the percentage of missed targets during a subject's attentional test. EOM is a measure of inattention.

As used herein, "errors of commission" or "EOC" or "commission errors" refers to the percentage of incorrect responses to non-targets during a subject's attentional test. EOC is a measure of impulsivity.

As used herein, "latency" or "LAT" refers to the average amount of time to respond correctly during a subject's attentional test (speed).

As used herein, "standard deviation of latency" or "LATSD" or "variability" or "variability in response latency"

refers to the standard deviation in the average amount of time to respond correctly during a subject's attentional test (standard deviation in speed).

As used herein, "coefficient of variation of latency" or "LATCV" or "C.O.V." refers to a normalized measure of response time variation (LATCV=LATSD/LAT).

As used herein, "number of attention shifts" or "shift" or "number of shifts" refers to the number of shifts in the attentional state of the subject observed during an attentional test. The number of shifts is a measure of how many times a change in behavioral states occurs over the course of a test.

As used herein, "percent time spent impulsive state" or "imp" or "impulsive" refers to the percent of blocks when the subject performed better than chance but made a significant number of commission errors. This metric is derived from the shifts in attentional state analysis of the subject's attentional test.

As used herein, "percent time spent in distracted state" or "distr" or "distracted" refers to the percent of blocks when the subject performed better than chance but missed a significant number of targets. This metric is derived from the shifts in attentional state analysis of the subject's attentional test.

As used herein, "percent time spent in random state" or "rand" or "random" refers to the percent of blocks when the subject performed no better than predicted by random chance. This metric is derived from the shifts in attentional state analysis of the subject's attentional test.

As used herein, "percent time spent in minimal response state" or "min" or "minimal" refers to the percent of blocks when the subject performed no better than predicted by random chance and made few responses. This metric is derived from the shifts in attentional state analysis of the subject's attentional test.

As used herein, "percent time spent in contrary response state" or "cont" or "contrary" refers to the percent of blocks when the subject performed worse than predicted by random chance. This metric is derived from the shifts in attentional state analysis of the subject's attentional test.

As used herein, "percent time spent in attentive state" or "attn" or "on-task" refers to the percent of blocks in which the subject performed with very high level of accuracy. This metric is derived from the shifts in attentional state analysis of the subject's attentional test.

As used herein, "adj-latency" or "accuracy-adjusted latency" refers to a composite score based upon latency, the variation in response time to the correct target during a subject's attentional test, and accuracy, the correct responses during a subject's attentional test. Accuracy-adjusted latency can be calculated as described in U.S. Patent Publication No. 20030233032, published Dec. 18, 2003, and incorporated herein by reference.

As used herein, "immobility time of head" or "h_imm" or "immobility duration" refers to the average amount of time spent sitting still according to data generated using the reflector placed on the subject's head.

As used herein, "area of head movements" or "h_area" or "area" refers to the total area covered by the marker's path according to data generated using the reflector placed on the subject's head.

As used herein, "temporal scaling exponent" or "h_temp" or "temporal scaling" refers to the pattern of movement in time according to data generated using the reflector placed on the subject's head. The temporal scaling exponent is calculated from the log-log reciprocal stochastic relationship between the frequency of microevents and their duration. For a two-process model in which a marker is either in motion or immobile, stochastic theory dictates that there will be a greater number of brief periods of immobility than long periods of immobility (though not necessarily a greater amount of time). The log-log relationship provides a robust measure of relative activity versus inactivity. Lower values indicate lack of movement, while higher values indicate incessant movement.

As used herein, "displacement" or "h_disp" refers to the total distance moved by the marker according to data generated using the reflector placed on the subject's head.

As used herein, "spatial scaling exponent" or "h_spat" or "spatial complexity" refers to the complexity of the marker movement path and is calculated by ascertaining the logarithmic rate of information decay at progressively lower levels of temporal resolution. Lower values indicate linear or back-and-forth movement, while higher values indicate more complex movement.

As used herein, "microevents" or "h_mic" or "movements" refers to the number of position changes according to data generated using the reflector placed on the subject's head. A new microevent begins whenever the marker moves 1.0 mm (or some other prespecified distance) or more from the location of the previous microevent, and it is defined by its position and duration. Microevents should be defined first, as all the other movement measures are derived from the microevent measures.

As used herein, "area of right and left shin movements" or "rl_area" refers to the average of the right and left total area covered by the marker's path according to data generated using reflectors placed on the subject's right and left shins.

As used herein, "rl_mic" refers to the average of the right and left number of position changes according to data generated using reflectors placed on the subject's right and left shins. A new microevent begins whenever the marker moves 1.0 mm (or some other prespecified distance) or more from the location of the previous microevent, and it is defined by its position and duration. Microevents should be defined first, as all the other movement measures are derived from the microevent measures.

As used herein, "rl_disp" refers to the average of the right and left total distance moved by the marker according to data generated using reflectors placed on the subject's right and left shins.

Other features and advantages of the invention will be apparent from the following detailed description and the claims.

BRIEF DESCRIPTION OF THE DRAWINGS

FIGS. 2A and 2B are drawings depicting motion data captured by a reflector attached to the head of a subject and various motor activity metrics extracted from the data for a subject having ADHD while unmedicated (FIG. 2A) and after medication with Adderall (FIG. 2B).

FIGS. 3A and 3B are drawings depicting attention data from a subject's responses to target and non-target stimuli and various attention metrics extracted from the data for a subject having ADHD while unmedicated (FIG. 3A) and after medication with Adderall (FIG. 3B).

FIGS. 4A and 4B are drawings depicting attention data from a subject's responses to target and non-target stimuli and attention metrics derived from a shifts in attentional state analysis of the data for a subject having ADHD while unmedicated (FIG. 4A) and after medication with Adderall (FIG. 4B).

FIGS. 5A and 5B are drawings depicting a form for reporting both concordance (i.e., a differential diagnosis of ADHD or subject classification using the concordance composite score) and the magnitude of attention disturbance (inattention), the magnitude of motor activity disturbance (high motion), and a global composite score (global scaled score). FIG. 5A is the result for the unmedicated subject, while FIG. 5B is the subject medicated with Adderall.

DETAILED DESCRIPTION

Figure 1:
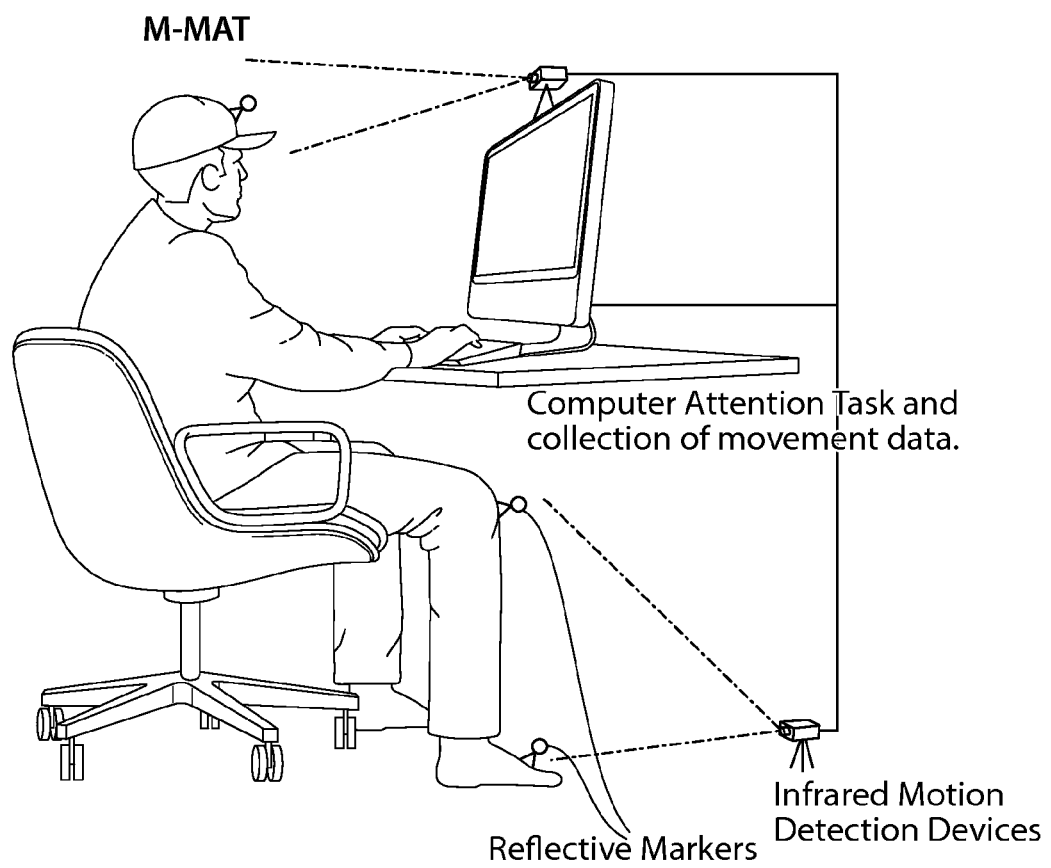
FIG. 1 is a picture depicting McLean Motion and Attention Test (M-MAT™), which is cleared by the FDA for assessment of the core symptoms of ADHD—hyperactivity, impulsivity and inattention. The M-MAT™ test results provide precise quantitative assessment of the capacity of children, adolescents and adults to pay attention to visual stimuli while inhibiting their locomotor activity and controlling their urge to respond impulsively. The test consists of an infrared motion analysis system, which tracks head movement in children (and head plus lower extremity movement in adolescents and adults), while they perform a monotonous but demanding novel Go/No-Go continuous performance attention task. Vertical and horizontal positions of the infrared reflective markers are recorded 50 times per second to a resolution of about 0.4 mm.
Figure 3B:
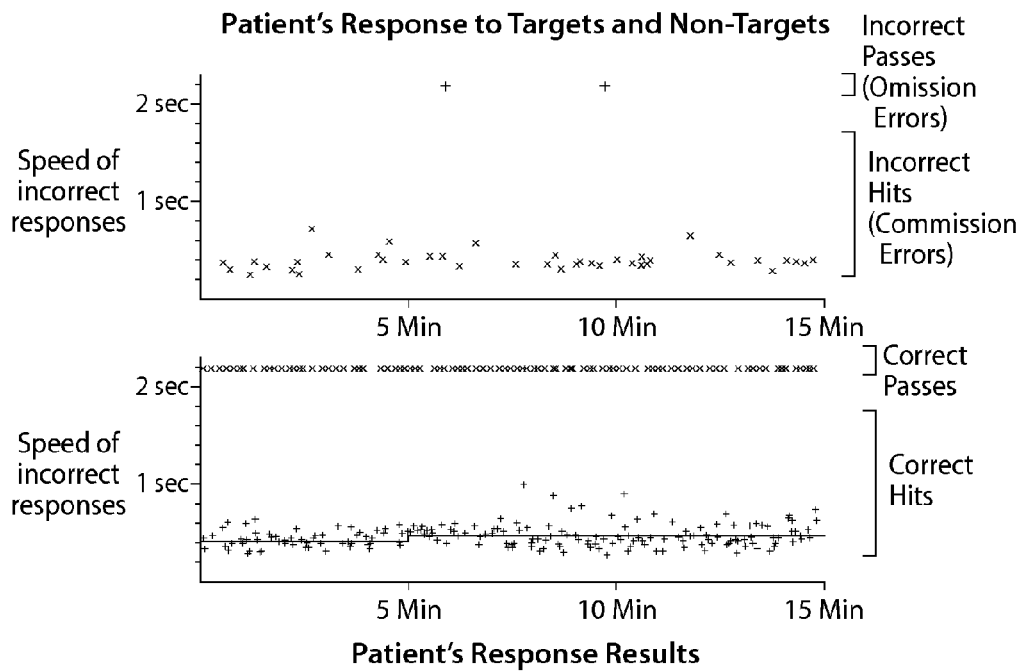
Figure 6:
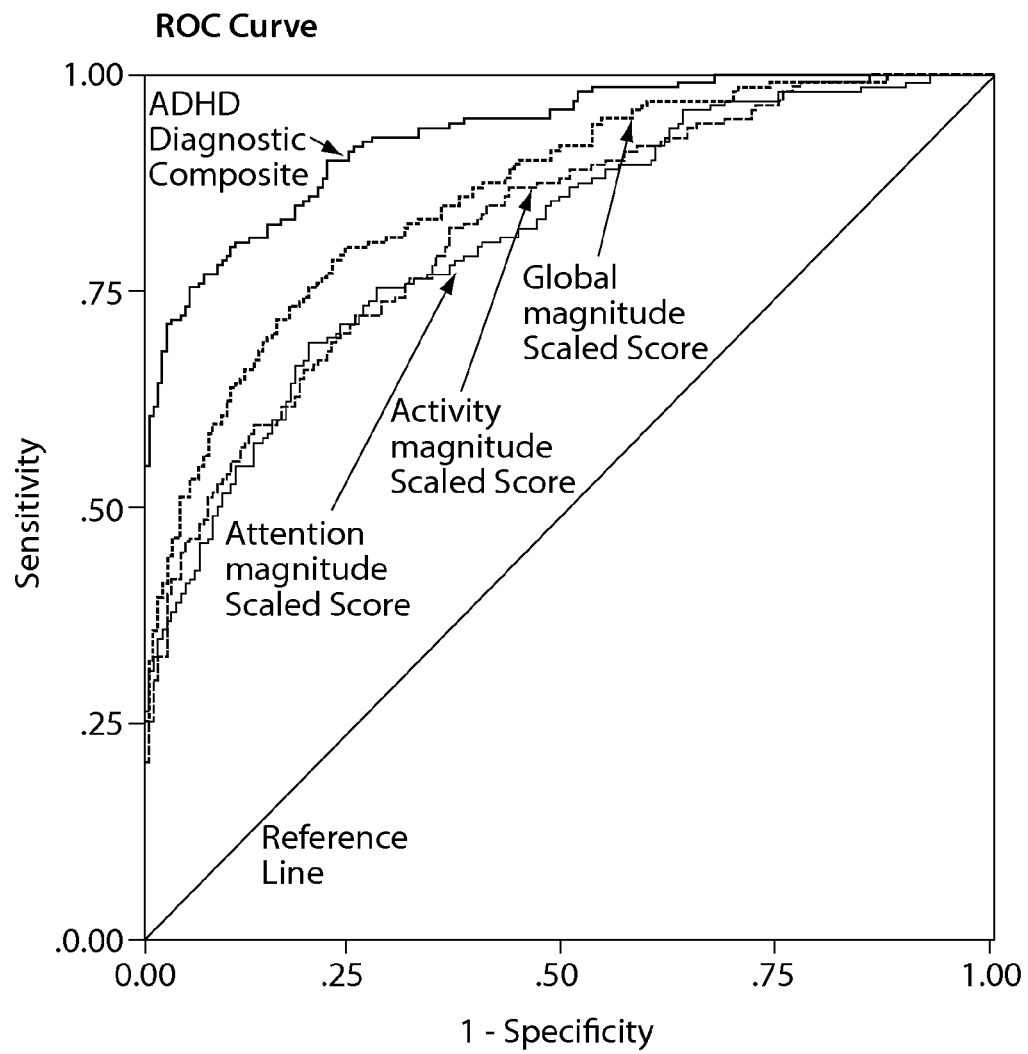
FIG. 6 is a graph of receiver operating characteristic (ROC) curves distinguishing between subjects with ADHD (n=144) and those without (n=707) (ROC analysis) based upon the concordance composite score (AUC=0.931±0.012), attention magnitude composite score (AUC=0.810±0.020), motor activity magnitude composite score (AUC=0.817±0.020) and global magnitude composite score (AUC=0.859±0.017).
Figure 7:
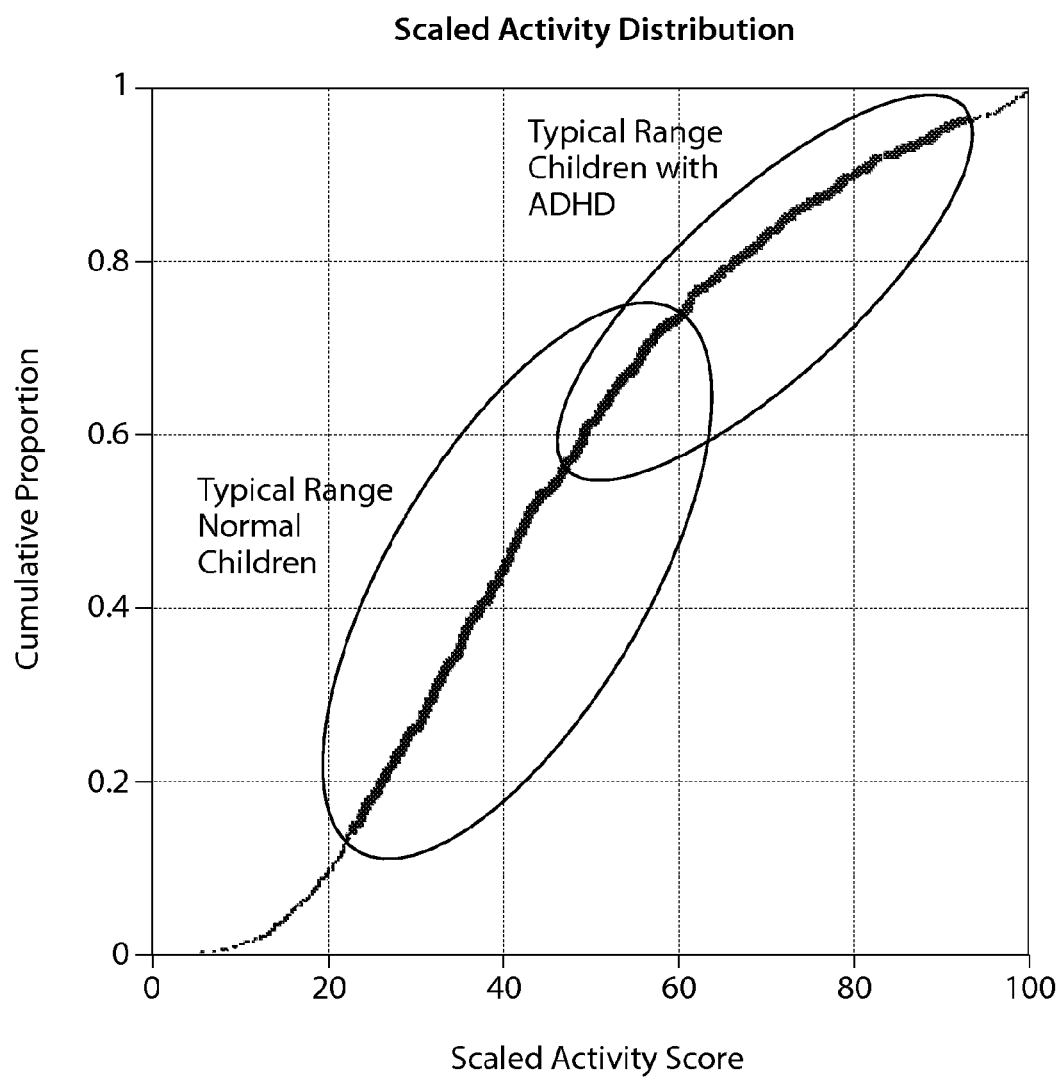
FIG. 7 is a graph depicting the distribution of normal and abnormal subjects in motor activity magnitude composite scores from equation 3 for a sample of 144 children with ADHD and 707 subjects from the community without ADHD. The distribution shows a gradation in response such that the inflection point between normal and abnormal subjects falls midway between the upper and lower bounds. Any change in a subject's magnitude of motor activity disturbance is easily observable as movement up and down the resulting curve. Note that there is some room below normal to show "overmedication" effects, and some room above ADHD to show severe worsening. A similar distribution is observed for the attention magnitude composite score and the global magnitude composite score.
Figure 8:
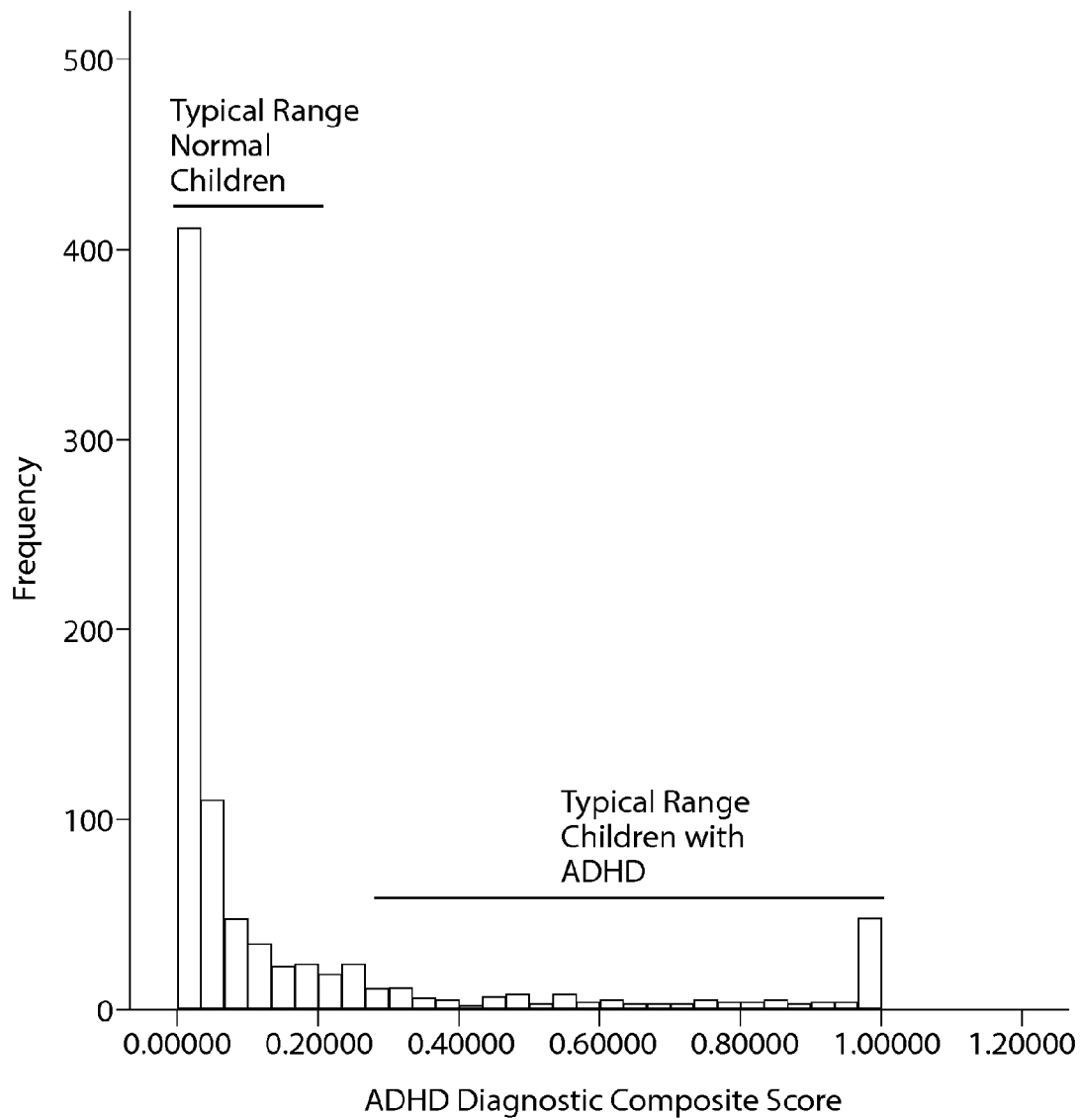
FIG. 8 is a graph depicting the distribution of normal and abnormal (ADHD) subjects in concordance composite scores from equation 1 for a sample of 144 children with ADHD and 707 subjects from the community without ADHD. The distribution shows little overlap between the normal and abnormal populations, as the normal subjects typically score near the lower limit and the abnormal subjects typically score near the upper limit. Such a distribution is desirable for the purpose of differential diagnosis, but not for monitoring change in a subject over time.
Figure 9:
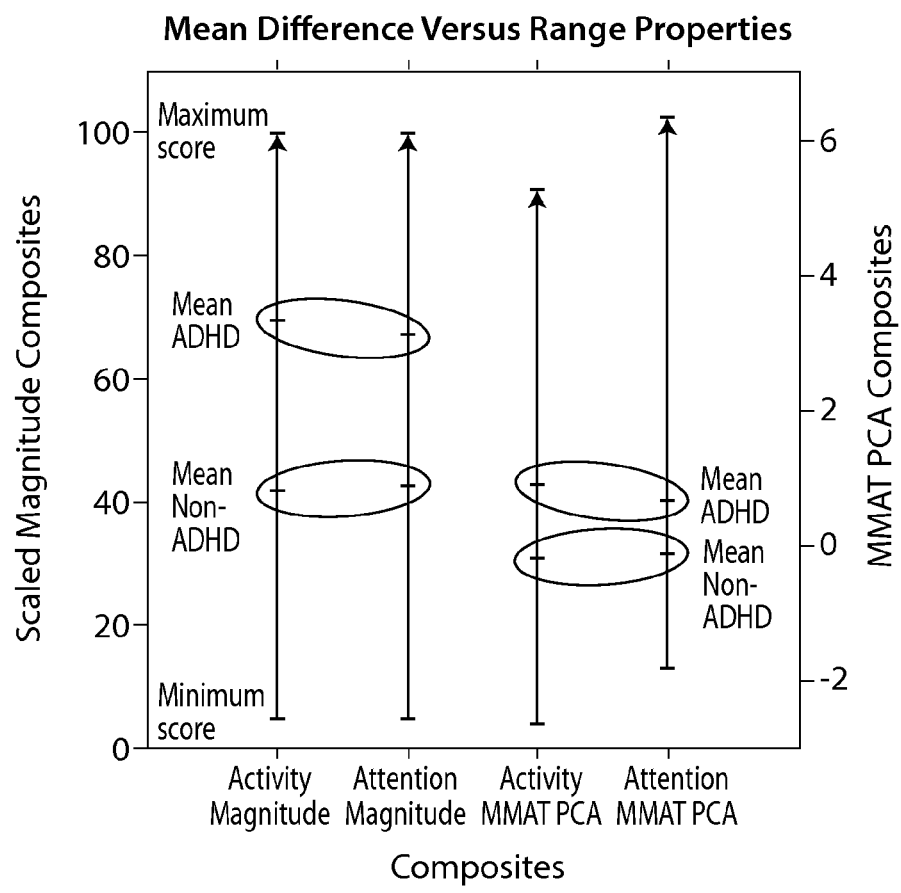
FIG. 9 is a graph depicting the difference between mean ADHD subjects and mean normal (Non-ADHD) subjects versus the range (highest score–lowest score) of observed scores for the following composites: (i) the magnitude of attention disturbance composite, (ii) the magnitude of motor activity disturbance composite, (iii) the M-MAT motor activity composite (derived using PCA, prior art), and (iv) the M-MAT attention composite (derived using PCA, prior art). These values were calculated from a sample of ADHD (n=144) and Non-ADHD (n=707) subjects. For the magnitude of disturbance composites of the invention the dynamic range between normal and abnormal subjects is large (i.e., ([mean abnormal–mean normal]/range)×100=25.5% for the magnitude of attention disturbance composite and 29.0% the magnitude of motor activity disturbance composite). In contrast, the M-MAT composites have a small dynamic range between normal and abnormal subjects (i.e., ([mean abnormal–mean normal]/range)×100=10.1% for the M-MAT attention composite and 13.9% the M-MAT motor activity composite). A larger dynamic range between normal and abnormal subjects is desirable to produce composite scores that are sensitive to changes in a subject (i.e., such as a modest improvement resulting from therapy, or a change in the subject over time) and readily interpretable clinically.

The invention features methods and systems to monitor changes in the magnitude of attentional disturbance and the magnitude of motor activity disturbance in a subject. The invention also features methods and systems for determining a subject's degree of concordance with individuals having an attentional disorder versus individuals not having an attentional disorder. The methods and systems of the invention can enable clinicians and consumers to ascertain both the severity of an attentional disorder as well as how much an individual changes over time, or with therapy.

Systems

The invention consists of a number of parts, including a client software program that runs the protocol and a software program for providing an evaluation according to the methods of the invention. For example, the test itself can consist of a computerized Go/No-Go attention task designed to determine shifts in attentional state (see U.S. Pat. No. 6,685,652) that is coupled to an infrared motion analysis system to record head movements as an index of hyperactivity.

Motion Detection System

A motion detection system can be used to track the movement of the head an/or lower extremities of the individual receiving a motor activity test. Movement patterns are analyzed using procedures described by Teicher et al., J. Am. Acad. Child Adolsec. Psychiatry 35:334 (1996), which are based on the concept of microevents. A new microevent begins whenever the marker moves more than a predetermined distance (e.g., 1.0 mm or more) from the location of the previous microevent, and is defined by its position and duration. From the sequence of microevents, the mean locomotor path length can be calculated, along with two scaling exponents.

The first exponent, the spatial scaling exponent, is a measure of the complexity of the movement and is calculated by ascertaining the logarithmic rate of information decay at progressively lower levels of resolution. Conceptually, if a marker is still or moving in a straight line, no information is lost if the marker's position is sampled less frequently. The total distance traversed can still be calculated. On the other hand, if a marker is moving in a convoluted path, then less frequent sampling smoothes out the route and underestimates the distance traveled. Spatial complexity corresponds to the concept of fractal dimensions and ranges from 1.0 (straight line movement) to 2.0 (complex, convoluted movement patterns).

The other exponent, known as the temporal scaling exponent, is calculated from the log-log relationship between the frequency of the microevents and their duration. For a two-process model in which a marker is either in motion or immobile, stochastic theory dictates that there will be a greater number of brief periods of immobility than long periods of immobility (though not necessarily a greater amount of time). The log-log relationship provides a robust measure of relative activity versus inactivity and indicates the degree to which a subject is moving in the environment.

Any video camera or other motion-sensing device capable of detecting the movements of the test subject can be used. For example, the motion analysis device can be an infrared motion analysis system (e.g., Qualisys, Glastonbury, Conn.) that includes a high-resolution CCD infrared video camera, an infrared strobe, and a video processor that provides hardware analysis of the video signal and outputs data to a computer. Such infrared motion analysis systems are known in the art, and are specifically designed to detect and record the precise vertical and horizontal position of small, light-weight infrared reflective markers. These markers are attached to the subject at various points, such as the head, shoulders, arms, legs, and feet. As the subject moves these portions of his or her body, the IR motion analysis system detects changes in the positions of the markers and relays this information to a computer. Successive marker coordinates can be stored in the computer and analyzed using commercially available software (e.g., M-MAT™ software). Desirably, the camera is positioned in front of the subject, who is preferably in a seated position. The camera is also desirably positioned in such a manner that it can capture movements of the reflective markers in three dimensions, including movements towards and away from the display device. The motion analysis device can also include a second camera that can be used in combination with the first camera to better differentiate three dimensional movement. Adults with ADHD can manifest hyperactivity solely through excess movement of their lower extremities while seated. Therefore, the first camera can be used to track the movement of the subject's legs and/or feet or a second camera can be used to track the movement of the subject's lower extremities while the first camera tracks upper body movements.

Attentional Testing

The attentional testing includes a cognitive control task, such as a continuous performance test (CPT), the results of which are diagnostic of physiological response to medication. For example, a subject's visual attention can be tested by displaying a series of visual stimuli, to which the subject is instructed to respond. Typically, the stimuli are of two types, and the subject is instructed to respond to only one of them. Data are collected for each stimulus presented including the type of stimulus, whether or not the subject responded, and if so, how long the subject took to respond. The continuous performance attention test has been in use since the mid 50's (Rosvold et al., J. Consulting and Clinical Psychology 20:343 (1956)), with computerized versions available in the 1970s (Greenberg, Psychopharmacol. Bull. 23:279 (1987)).

The CPT results can include measuring errors of commission, errors of omission, and mean correct reaction time with standard deviation. More sophisticated CPT measures, derived from signal detection theory can include a calculation of stimulus sensitivity (d') (see, for example, Nuechterlein, J. Abnorm. Psychol. 92:4 (1983)).

Analysis of the CPT results can also include assessing the pattern or fluctuation in attentional states by a subject during a test period. This approach is described in U.S. Pat. No. 6,685,652, incorporated herein by reference.

The methods of the invention may be used alone, together, or in conjunction with other well-known psychological tests for determining attention or reaction time. Testing of the subject's performance may be conducted with or without providing corrective feedback to the subject during performance of the CPT.

At the end of the testing, the recorded data (e.g., attentional test data and/or motion data) can be processed by a local computer or transmitted over a computer network to a central station for processing. A report can be generated at the testing site, or at the site of remote processing. Such a report may be in a paper form, electronic form, or stored in a database as part of the subject's medical records. The report can include one or more of the following: (i) the unmedicated and medicated results for two or more tests belonging to a test subject; (ii) the results obtained for a test subject and the range of results observed for normal subjects given the subject's gender, age, and/or grade; (iii) the identification of a test subject as normal or having an attentional disorder; (iv) the identity of the drug used to produce medicated test results; (v) the magnitude of attention disturbance for the test subject; (vi) the magnitude of motor activity disturbance for the test subject; (vii) the global composite score for the test subject; and/or (viii) the concordance composite score for the test subject.

The following example is put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Degree of Concordance

The degree of concordance is calculated using formula 1. This formula compares the test subject to individuals known to have an attentional disorder, such as ADHD, and to normal subjects. The present example is a formula for evaluating the degree of concordance with ADHD subjects.

The concordance composite score reports, on a 0-100 scale (higher number means stronger correlation), the extent to which the pattern of, in this case, 19 measures for the tested patient correlate, at the high end of the scale, with the pattern of measures for individuals known to have ADHD, and correlate, at the low end of the scale, with the pattern of measures for individuals known to be normal.

Formula (1) is the result of a logistic regression analysis, which provides a fit in the form of y (degree of concordance) $=x/(1+x)$. In formula (1) SEX is either 1 (male) or 2 (female).

$$\text{Degree of concordance} = x/(1+x), \quad (1)$$

where  x=32.018249507531+AGE*1.11794465464208+ SEX*−0.633566744482312+ACC*−0.41463891228142+ EOM*−0.0694910554539715+EOC*− 0.222261396361939+LAT*0.00550061328954941+ LATSD*0.010757983969629+ LATCV*0.01543921959046050+ H_IMM*3.86743605465514+H_MIC*− 0.00134516549758059+H_DISP*0.705431868641794+ H_AREA*0.00415700825672488+H_SPAT*− 8.18153866756578+H_TEMP*2.08700211410285+ SHIFT*−0.0107055462853913+ ATTN*0.110192756777774+DISTR*1.17170140315258+ IMP*0.0018909218909202+RAND*0.204550300923093+ MIN*4.3806099363172+CONT*−11.3921076208079

EXAMPLE 2

Magnitude of Attention Disturbance and Magnitude of Motor Activity Disturbance

The magnitude of motor activity disturbance and magnitude of attention disturbance scores compare the test subject to a community database of age matched subjects representing a cross section of the general population on the dimensions of activity and inattention, respectively.

The present example includes formulas for calculating a magnitude of attention disturbance and a magnitude of motor activity disturbance, which are useful for monitoring changes in the severity of inattention and hyperactivity in ADHD subjects.

The magnitude disturbance scores utilize a subset of measures that have linear scaling properties and were found to be particularly responsive to treatment. These scores are reported, for example, on a 0-100 scale, which correspond approximately to composite percentile rank for subjects of similar age and gender. For example a higher score indicates that the subject has greater motion or inattention than most individuals for similar age and gender and conversely, a lower score reflects less movement or inattention than most of the community sample. The magnitude composite scores are specifically designed to measure change associated with treatment.

Equation 2 provides the magnitude of attention disturbance and equation 3 provides the magnitude of motor activity disturbance. In these formulas sex is either 1 (male) or 2 (female).

Inattention severity composite, Inattention Scaled Score for children 6-14 years (reported)

$$\text{Attention magnitude composite score} = \text{Inattention} = 100 + (-100/(\text{EXP}(0.00669558245922736*(\text{age}*3.80993619841975 - (9.79872637063541*\text{gender} - 7.94834522732847*eom - 0.632107326313438*latsd + 0.103761205697897*\text{adj-latency} - 217.435581312475*(\text{Distracted} + \text{Minimal}))))) \quad (2)$$

Activity severity composite, Activity Scaled Score for children 6-14 years (reported)

$$\text{Motor activity magnitude composite score} = 100 + (-100/(\text{EXP}(0.017695045*(\text{age}*1.13722492676889 - (4.31506717792978*\text{gender} + 0.010600166*\text{micro} - 15.032412641646*\text{displ} - 0.145286531675578*\text{area})))) \quad (3)$$

A global composite score can also be reported. For example, the ADHD "severity" composite, the global scaled score, is simply an average of the magnitude of motor activity disturbance and magnitude of attention disturbance from equations 2 and 3 above.

EXAMPLE 3

Magnitude of Attention Disturbance and Magnitude of Motor Activity Disturbance in Adults The formulas for magnitude composites for adults are similar to the ones for children, but are not necessarily identical. For example, the magnitude of motor activity disturbance composite for adults can include shin data in addition to head data (see equation 5).

Inattention severity composite, Inattention Scaled Score for adults (reported)

$$\text{Adult Attention magnitude composite score} = \text{Inattention Score} = 100 + (-100/\exp(0.0162438179974398*(\text{age}* - 0.283274725059185 - (5.91311283064259*\text{Gender} - 8.31839189524816*eom - 0.0897300642446829*lat\_var - 0.332003923539837*LATCV + - 94.2788241826255*\text{distr} - 1957.37902391527*\text{Min})))) \quad (4)$$

Activity severity composite, Activity Scaled Score for adults (reported)

$$\text{Adult Motor activity magnitude composite score} = 100 + (-100/\exp(0.00422156971437696*(\text{age}* - 0.162873991940596 - (17.2198415142961*\text{gender} - 0.0241996250978854*h\_\text{micro} - 13.7915074622364*h\_\text{disp} - 0.293580293514179*h\_\text{area} + 0.0314755990292945*rl\_\text{micro} - 30.2407045191884*rl\_\text{disp} - 1.00780039930657*rl\_\text{area})))) \quad (5)$$

Additional formulas for magnitude composites for adults are provided in equations 6 and 7 (below).

$$\text{Adult Motor activity magnitude composite score} = \text{Scaled Activity Severity Score} = 100 + (-100/\exp(0.0267854402381704*(\text{age}* - 0.275867434424546 - (5.93886226417483*\text{Gender} - 1.11145907408907*\text{Head\_norm\_Intermed} - 0.265432910182478*\text{Leg\_norm\_Intermed}))). \quad (6)$$

In equation 6, Head_norm_Intermed and Leg_norm_Intermed are calculated as shown in equations 6a and 6b and CDF_Normal is a normal cumulative distribution function.

$$\text{Head\_norm\_Intermed} = 100*\text{CDF\_Normal}(-1.139 + 0.000289*h\_mic + 0.145*h\_\text{disp} + 0.00318*h\_\text{area}); \text{ and} \quad (6a)$$

$$\text{Leg\_norm\_Intermed} = 100*\text{CDF\_Normal}(-0.638 + 0.0005161*rl\_mic + 0.268rl\_\text{disp} + 0.01181*rl\_\text{area}) \quad (6b)$$

$$\text{Adult Attention magnitude composite score} = \text{Scaled Attention Severity Score} = 100 + (-100/\exp(0.00970101036295301*(\text{age}* - 0.853901739589225 - (9.33755459195823*\text{Gender} - 2.04350545909847*\text{distr\_norm\_Intermed} - 0.88015812938208*\text{effort\_norm\_Intermed})))) \quad (7)$$

In equation 7, distr_norm_intermed and effort_norm_intermed are calculated as shown in equations 7a and 7b and CDF_Normal is a normal cumulative distribution function.

$$\text{distr\_norm\_intermed} = 100*\text{CDF\_Normal}(-3.108 - 4.706E-02*EOM + 3.964E-04*EOC + 2.838E-03*LAT + 5.542E-03*LATSD + 1.901E-02*LATCV + 4.686E-02*\text{SHIFT} - 0.689*\text{ATTN} + 2.734*DISTR + 2.514*\text{RAND} + -4.862*\text{MIN}) \quad (7a)$$

$$\text{effort\_norm\_intermed} = 100*\text{CDF\_Normal}(-0.673 + 0.141*EOM - 1.301E-03*EOC - 2.396E-05*LAT + 1.706E-03*LATSD + 1.153E-02*LATCV - 2.163E-02*\text{SHIFT} + 0.778*\text{ATTN} - 0.761*\text{DISTR} + 3.104*\text{RAND} + 10.813*\text{MIN}) \quad (7b)$$

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for evaluating a subject, said method comprising:
   (a) testing said subject to produce test data; and
   (b) transmitting said test data to a computer for analysis, wherein said analysis comprises (i) extracting from said test data values for responsive attention metrics and values for responsive motor activity metrics; (ii) calculating from said responsive attention metrics a magnitude of attention disturbance in said subject, wherein said magnitude of attention disturbance (iia) is a score calculated from a composite formula that scores a subject according to attention performance utilizing said responsive attention metrics; (iib) is calculated from a composite formula that yields a large dynamic range between normal and untreated Attention-Deficit/Hyperactivity Disorder (ADHD) subjects, such that the difference in the mean of distributions of magnitude of attention disturbance scores for normal and untreated ADHD subjects is 20% to 50% of a theoretical range for a bounded scale or 25% to 50% of the observed range for a non-bounded scale; and (iic) the magnitude of attention disturbance score is responsive to medication in an ADHD subject in a graded manner; (iii) calculating from said responsive motor activity metrics, the magnitude of motor activity disturbance in said subject, wherein said magnitude of motor activity disturbance (iiia) is a score calculated from a composite formula that scores a subject according to motor activity performance utilizing said responsive motor activity metrics; (iiib) is calculated from a composite formula that yields a large dynamic range between normal and untreated ADHD subjects, such that the difference in the mean of distributions of magnitude of motor activity disturbance scores for normal and untreated ADHD subjects is 20% to 50% of a theoretical range for a bounded scale or 25% to 50% of the observed range for a non-bounded scale; and (iiic) the magnitude of motor activity disturbance score is responsive to medication in an ADHD subject in a graded manner; and (iv) on the basis of said magnitude of attention disturbance and said magnitude of motor activity disturbance evaluating said subject, wherein said testing comprises measuring the activity of said subject using an infrared motion analysis system by tracking the movements of said subject's head, leg, or foot using a camera and said test data comprises motor activity data.

2. The method of claim 1, wherein said analysis further comprises (x) extracting from said test data values for attention metrics and values for motor activity metrics; (y) calculating from said attention metrics and said motor activity metrics a concordance composite score; and (z) on the basis of said concordance composite score determining the probability of said subject having an attentional disorder.

3. The method of claim 2, wherein said analysis further comprises, based upon said concordance composite score, determining whether said subject has said attentional disorder.

4. The method of claim 2, wherein said analysis further comprises classifying said subject on the basis of said probability.

5. The method of claim 4, wherein said classifying comprises identifying said subject as having a very low, low, medium, or high probability of said subject having said attentional disorder.

6. The method of claim 2, wherein said attentional disorder is Attention Deficit Disorder, Attention Deficit Hyperactivity Disorder, or Hyperkinetic Disorder.

7. The method of claim 1, wherein said method is repeated to observe changes in the magnitude of attention disturbance, the magnitude of motor activity disturbance, or the global composite score of said subject.

8. The method of claim 7, wherein said changes result from aging.

9. The method of claim 7, wherein said changes result from therapy.

10. The method of claim 9, wherein said testing is performed on said subject while unmedicated and while medicated.

11. The method of claim 1, wherein said testing comprises performing an attentional test on said subject and said test data comprises attentional data.

12. The method of claim 11, wherein said analysis comprises assessing the fluctuation in attentional states of said subject.

13. The method of claim 1, wherein said responsive attention metrics are attention metrics indicative of distraction or attention metrics indicative of diminished effort.

14. The method of claim 13, wherein said responsive attention metrics are selected from errors of omission, percent time spent in distracted state, percent time spent in minimal response state, accuracy-adjusted latency, and variability in response latency.

15. The method of claim 1, wherein said magnitude of motor activity disturbance is calculated from a composite that comprises motor activity metrics, wherein said motor activity metrics consist of responsive motor activity metrics.

16. The method of claim 15, wherein said responsive motor activity metrics are selected from microevents, displacement, and area.

17. The method of claim 1, further comprising calculating from said magnitude of attention disturbance and said magnitude of motor activity disturbance a global composite score; and on the basis of said global composite score evaluating said subject.

18. The method of claim 1, wherein said magnitude of attention disturbance is calculated from a composite that does not comprise attention metrics indicative of impulsivity.

19. The method of claim 1, wherein said attention metrics indicative of impulsivity are selected from errors of commission and percent time spent in impulsive state.

20. The method of claim 1, wherein said magnitude of attention disturbance is calculated from a composite that comprises at least two, three, four, or five responsive attention metrics.

21. The method of claim 1, wherein said magnitude of attention disturbance is calculated from a composite that comprises attention metrics, wherein said attention metrics consist of responsive attention metrics.

22. The method of claim 1, wherein said magnitude of motor activity disturbance is calculated from a composite that comprises at least two or three responsive motor activity metrics.

23. The method of claim 1, wherein said magnitude of attention disturbance is calculated from a composite formula that yields (i) an effect size in the distributions of magnitude of attention disturbance scores for normal and untreated ADHD subjects of from 0.8 to 4.0; (ii) an effect size in the distributions of normal and partially treated ADHD subjects of from 0.2 to 0.8; (iii) an effect size in the distributions of partially treated ADHD subjects and untreated ADHD subjects of from 0.2 to 0.8; and (iv) an effect size in the distributions of normal subjects and fully treated ADHD subjects of from −0.6 to +0.2.

24. The method of claim 1, wherein said magnitude of motor activity disturbance is calculated from a composite formula that yields (i) an effect size in the distributions of magnitude of motor activity disturbance scores for normal and untreated ADHD subjects of from 0.8 to 4.0; (ii) an effect size in the distributions of normal and partially treated ADHD subjects of from 0.2 to 0.8; (iii) an effect size in the distributions of partially treated ADHD subjects and untreated ADHD subjects of from 0.2 to 0.8; and (iv) an effect size in the distributions of normal subjects and fully treated ADHD subjects of from −0.6 to +0.2.

25. The method of claim 1, wherein said magnitude of attention disturbance, said magnitude of motor activity disturbance, or said global composite score is used to evaluate the efficacy of a therapy.

26. The method of claim 1, further comprising preparing a report providing an evaluation for the subject, said report comprising (i) the magnitude of attention disturbance score for said subject; and (ii) the magnitude of motor activity disturbance score for said subject.

27. A method for evaluating a subject, said method comprising:
(a) providing data having been collected by testing said subject to produce test data; and
(b) performing an analysis, said analysis comprising (i) extracting from said test data values for responsive attention metrics and values for responsive motor activity metrics; (ii) calculating from said responsive attention metrics a magnitude of attention disturbance in said subject, wherein said magnitude of attention disturbance (iia) is a score calculated from a composite formula that scores a subject according to attention performance utilizing said responsive attention metrics; (iib) is calculated from a composite formula that yields a large dynamic range between normal and untreated ADHD subjects, such that the difference in the mean of distributions of magnitude of attention disturbance scores for normal and untreated ADHD subjects is 20% to 50% of a theoretical range for a bounded scale or 25% to 50% of the observed range for a non-bounded scale; and (iic) the magnitude of attention disturbance score is responsive to medication in an ADHD subject in a graded manner; (iii) calculating from said responsive motor activity metrics, the magnitude of motor activity disturbance in said subject, wherein said magnitude of motor activity disturbance (iiia) is a score calculated from a composite formula that scores a subject according to motor activity performance utilizing said responsive motor activity metrics; (iiib) is calculated from a composite formula that yields a large dynamic range between normal and untreated ADHD subjects, such that the difference in the mean of distributions of magnitude of motor activity disturbance scores for normal and untreated ADHD subjects is 20% to 50% of the theoretical range for a bounded scale or 25% to 50% of a observed range for a non-bounded scale; and (iiic) the magnitude of motor activity disturbance score is responsive to medication in an ADHD subject in a graded manner; and (iv) on the basis of said magnitude of attention disturbance and said magnitude of motor activity disturbance evaluating said subject, wherein said testing comprises measuring the activity of said subject using an infrared motion analysis system by tracking the movements of said subject's head, leg, or foot using a camera and said test data comprises motor activity data.

28. A method for evaluating a subject, said method comprising:
(a) testing said subject to produce test data; and
(b) transmitting said test data to a computer for analysis, wherein said analysis comprises (i) extracting from said test data values for responsive attention metrics and values for responsive motor activity metrics; (ii) calculating from said responsive attention metrics a magnitude of attention disturbance in said subject; and (iii) calculating from said responsive motor activity metrics a magnitude of motor activity disturbance in said subject; and
(c) extracting from said test data values for attention metrics and values for motor activity metrics; calculating from said attention metrics and said motor activity metrics a concordance composite score; and on the basis of said concordance composite score determining the probability of said subject having an attentional disorder,
wherein said concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state, wherein said testing comprises measuring the activity of said subject using an infrared motion analysis system by tracking the movements of said subject's head, leg, or foot using a camera and said test data comprises motor activity data.

29. A system for evaluating a subject, said system comprising:
(a) an input component configured to receive test data for said subject; and
(b) a processor provided with a computer program for (i) extracting from said test data values for responsive attention metrics and values for responsive motor activity metrics; (ii) calculating from said responsive attention metrics a magnitude of attention disturbance in said subject, wherein said magnitude of attention disturbance (iia) is a score calculated from a composite formula that scores a subject according to attention performance utilizing said responsive attention metrics; (iib) is calculated from a composite formula that yields a large dynamic range between normal and untreated ADHD subjects, such that the difference in the mean of distributions of magnitude of attention disturbance scores for normal and untreated ADHD subjects is 20% to 50% of a theoretical range for a bounded scale or 25% to 50% of the observed range for a non-bounded scale; and (iic) the magnitude of attention disturbance score is responsive to medication in an ADHD subject in a graded manner; and (iii) calculating from said responsive motor activity metrics a magnitude of motor activity disturbance in said subject, wherein said magnitude of motor activity disturbance (iiia) is a score calculated from a composite formula that scores a subject according to motor activity performance utilizing said responsive motor activity metrics; (iiib) is calculated from a composite formula that yields a large dynamic range between normal and untreated ADHD subjects, such that the difference in the mean of distributions of magnitude of motor activity disturbance scores for normal and untreated ADHD subjects is 20% to 50% of a theoretical range for a bounded scale or 25% to 50% of the observed range for a non-bounded scale; and (iiic) the magnitude of motor activity disturbance score is responsive to medication in an ADHD subject in a graded manner, wherein said testing comprises measuring the activity of said subject using an infrared motion analysis system by tracking the movements of said subject's head, leg, or foot using a camera and said test data comprises motor activity data.

30. A method for evaluating a subject, said method comprising:
  (a) testing said subject to produce test data; and
  (b) transmitting said test data to a computer for analysis, wherein said analysis comprises (i) extracting from said test data values for attention metrics and values for motor activity metrics; (ii) calculating from said attention metrics and said motor activity metrics a concordance composite score; and (iii) on the basis of said concordance composite score determining the probability of said subject having an attentional disorder,
  wherein said concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state, wherein said testing comprises measuring the activity of said subject using an infrared motion analysis system by tracking the movements of said subject's head, leg, or foot using a camera and said test data comprises motor activity data.

31. A method for evaluating a subject, said method comprising:
  (a) providing data having been collected by testing said subject to produce test data; and
  (b) performing an analysis, said analysis comprising (i) extracting from said test data values for attention metrics and values for motor activity metrics; (ii) calculating from said attention metrics and said motor activity metrics a concordance composite score; and (iii) on the basis of said concordance composite score determining the probability of said subject having an attentional disorder,
  wherein said concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state, wherein said testing comprises measuring the activity of said subject using an infrared motion analysis system by tracking the movements of said subject's head, leg, or foot using a camera and said test data comprises motor activity data.

32. A system for evaluating a subject, said system comprising:
  (a) an input component configured to receive test data for said subject; and
  (b) a processor provided with a computer program for (i) extracting from said test data values for attention metrics and values for motor activity metrics; and (ii) calculating from said attention metrics and said motor activity metrics a concordance composite score,
  wherein said concordance composite score is calculated from attention metrics and motor activity metrics selected from accuracy on the attention test, errors of omission, errors of commission, latency, standard deviation of latency, coefficient of variation of latency, immobility time of head, microevents, displacement, area of head movements, spatial scaling exponent, temporal scaling exponent, number of attention shifts, percent time spent in attentive state, percent time spent in distracted state, percent time spent impulsive state, percent time spent in random state, percent time spent in minimal response state, and percent time spent in contrary response state, wherein said testing comprises measuring the activity of said subject using an infrared motion analysis system by tracking the movements of said subject's head, leg, or foot using a camera and said test data comprises motor activity data.

* * * * *